United States Patent
King et al.

(10) Patent No.: US 10,191,039 B2
(45) Date of Patent: *Jan. 29, 2019

(54) HUMAN FACTOR XIII AS A NORMALIZATION CONTROL FOR IMMUNOASSAYS

(71) Applicant: Bio-Rad Laboratories, Inc., Hercules, CA (US)

(72) Inventors: David King, Benicia, CA (US); William F. Link, El Cerrito, CA (US); Renato del Rosario, Benicia, CA (US); Michael Leos, Fairfield, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/710,334

(22) Filed: Sep. 20, 2017

(65) Prior Publication Data

US 2018/0011093 A1    Jan. 11, 2018

Related U.S. Application Data

(60) Continuation of application No. 15/492,905, filed on Apr. 20, 2017, now Pat. No. 9,797,902, which is a division of application No. 13/922,821, filed on Jun. 20, 2013, now Pat. No. 9,658,220.

(60) Provisional application No. 61/663,293, filed on Jun. 22, 2012.

(51) Int. Cl.
| | |
|---|---|
| *G01N 31/00* | (2006.01) |
| *G01N 33/53* | (2006.01) |
| *G01N 33/543* | (2006.01) |
| *G01N 33/569* | (2006.01) |
| *C12N 9/10* | (2006.01) |
| *C12N 11/14* | (2006.01) |

(52) U.S. Cl.
CPC ......... *G01N 33/543* (2013.01); *C12N 9/1044* (2013.01); *C12N 11/14* (2013.01); *C12Y 203/02013* (2013.01); *G01N 33/54393* (2013.01); *G01N 33/56988* (2013.01)

(58) Field of Classification Search
CPC .............. G01N 33/96; G01N 33/543; G01N 33/54393; G01N 33/56988; G01N 2333/9108; G01N 435/973
See application file for complete search history.

(56) References Cited

U.S. PATENT DOCUMENTS

| | | | | |
|---|---|---|---|---|
| 6,261,762 | B1 | 7/2001 | Alizon et al. | |
| 6,660,486 | B2* | 12/2003 | Binder | G01N 33/96 |
| | | | | 435/287.2 |
| 6,916,621 | B2* | 7/2005 | Shah | C12Q 1/6809 |
| | | | | 435/174 |
| 7,141,362 | B2* | 11/2006 | Binder | G01N 33/96 |
| | | | | 435/4 |
| 7,608,465 | B2* | 10/2009 | Watkins | G01N 33/78 |
| | | | | 422/504 |
| 7,851,209 | B2 | 12/2010 | Wei et al. | |
| 8,137,987 | B2 | 3/2012 | Link et al. | |
| 9,658,220 | B2* | 5/2017 | King | G01N 33/543 |
| 9,797,902 | B2* | 10/2017 | King | G01N 33/56988 |
| 2003/0186250 | A1 | 10/2003 | Shah | |
| 2005/0239108 | A1 | 10/2005 | Barletta et al. | |
| 2009/0023164 | A1 | 1/2009 | Golding et al. | |

FOREIGN PATENT DOCUMENTS

| | | |
|---|---|---|
| CN | 1256695 A | 6/2000 |
| CN | 101266246 A | 9/2008 |
| EP | 1424086 A1 | 6/2004 |
| EP | 2322926 A1 | 5/2011 |
| JP | H04250167 A | 9/1992 |
| WO | 96/12809 A2 | 5/1996 |

OTHER PUBLICATIONS

Standeven et al. (Diabetes, Jan. 2002, vol. 51, No. 1, pp. 189-197).*
International Search Report and Written Opinion dated Nov. 15, 2013 for PCT Patent Application No. PCT/US2013/46878, 15 pages.
Lin et al., "Development of a sensitive, rapid, biotin-streptavidin based chemiluminescent enzyme immunoassay for human thyroid stimulating hormone", 2008, *Talanta*, vol. 75, No. 4, pp. 965-972.
Swanson et al., "Molecular Characterization of 39 HIV-1 Isolates Representing Group M (Subtypes A-G) and Group O: Sequence Analysis of gag p24, pol Integrase, and env gp41", 2003, *AIDS Research and Human Retroviruses*, vol. 19, No. 7, pp. 625-629.
First Office Action and Search Report dated Jul. 28, 2015 for Chinese Patent Application No. 201380035093.5, with English translation, 39 pages.
Supplementary European Search Report for European Application No. 13806909, dated Jan. 14, 2016, 14 pages.
Extended European Search Report dated Nov. 7, 2017 in EP Patent Application No. 17191779.2. 13 pages.
Blanchy, B.G. et al.; "Immobilization of factor XIII on collagen membranes"; Journal of Biomedical Materials Research; 1986; vol. 20; pp. 469-479.
Hormann, Helmut et al.; "N-Terminal Fibronectin 30-kDa Fragment Mediates the Immobilization of Soluble Fibrin by Factor XIIIa-Coated Polystyrene Beads"; Biological Chemistry Hoppe-Seyler; Jun. 1987; vol. 368; pp. 669-674.

\* cited by examiner

*Primary Examiner* — Lisa V Cook

(74) *Attorney, Agent, or Firm* — Kilpatrick Townsend & Stockton LLP

(57) ABSTRACT

The present disclosure provides compositions and methods that are useful for normalizing the amount of signal detected in an assay, such as an immunoassay. The compositions and methods are useful for improving the accuracy of immunoassays, such as immunoassays that detect whether a subject is infected with a retrovirus such as HIV.

12 Claims, 7 Drawing Sheets

Specification includes a Sequence Listing.

SEQUENCE LISTING

<160> NUMBER OF SEQ ID NOS: 5

<210> SEQ ID NO 1

```
<211> LENGTH: 33
<212> TYPE: PRT
<213> ORGANISM: Artificial Sequence
<220> FEATURE:
<223> OTHER INFORMATION: Synthetic protein

<400> SEQUENCE: 1

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Phe
            20                  25                  30

Asn

<210> SEQ ID NO 2
<211> LENGTH: 22
<212> TYPE: PRT
<213> ORGANISM: Artificial Sequence
<220> FEATURE:
<223> OTHER INFORMATION: Synthetic protein

<400> SEQUENCE: 2

Leu Asn Gln Gln Arg Leu Leu Asn Ser Trp Gly Cys Lys Gly Arg Leu
1               5                   10                  15

Val Cys Tyr Thr Ser Val
            20

<210> SEQ ID NO 3
<211> LENGTH: 24
<212> TYPE: PRT
<213> ORGANISM: Artificial Sequence
<220> FEATURE:
<223> OTHER INFORMATION: Synthetic protein

<400> SEQUENCE: 3

Lys Lys Leu Asn Gln Gln Arg Leu Leu Asn Ser Trp Gly Cys Lys Gly
1               5                   10                  15

Arg Leu Val Cys Tyr Thr Ser Val
            20

<210> SEQ ID NO 4
<211> LENGTH: 28
<212> TYPE: PRT
<213> ORGANISM: Artificial Sequence
<220> FEATURE:
<223> OTHER INFORMATION: Synthetic protein

<400> SEQUENCE: 4

Lys Tyr Leu Gln Asp Gln Ala Arg Leu Asn Ser Trp Gly Cys Ala Phe
1               5                   10                  15

Arg Gln Val Cys His Thr Thr Val Pro Phe Val Asn
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic protein
```

```
<400> SEQUENCE: 5

Arg Val Thr Ala Ile Glu Lys Tyr Leu Gln Asp Gln Ala Arg Leu Asn
1               5                   10                  15

Ser Trp Gly Cys Ala Phe Arg Gln Val Cys
            20                  25
```

HUMAN FACTOR XIII AS A NORMALIZATION CONTROL FOR IMMUNOASSAYS

CROSS-REFERENCES TO RELATED APPLICATIONS

This application is a continuation of U.S. patent application Ser. No. 15/492,905, now U.S. Pat. No. 9,797,902, entitled "HUMAN FACTOR XIII AS A NORMALIZATION CONTROL FOR IMMUNOASSAYS," filed on Apr. 20, 2017, which is a divisional of U.S. patent application Ser. No. 13/922,821, entitled "HUMAN FACTOR XIII AS A NORMALIZATION CONTROL FOR IMMUNOASSAYS," filed on Jun. 20, 2013, now U.S. Pat. No. 9,658,220, which claims the benefit of U.S. Provisional Patent Application No. 61/663,293, entitled "HUMAN FACTOR XIII AS A NORMALIZATION CONTROL FOR IMMUNOASSAYS," filed on Jun. 22, 2012, each of which are herein incorporated by reference in their entirety for all purposes.

FIELD OF THE INVENTION

This invention resides in the field of immunodiagnostics.

REFERENCE TO A "SEQUENCE LISTING," A TABLE, OR A COMPUTER PROGRAM LISTING APPENDIX SUBMITTED ON A COMPACT DISK

The Sequence Listing written in file 095191-094530US-1062021_SequenceListing.txt created on Sep. 19, 2017, 2,072 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

Immunoassays that detect HIV antigens and antibodies directed against HIV antigens in biological samples are useful to determine if a subject is infected with or has been exposed to HIV. Current assays detect HIV antigens and antibodies to HIV-1, including groups O and M, and antibodies to HIV-2. However, assays that detect the amount of analytes in a biological sample are subject to errors that can produce spurious results. There are numerous factors that can produce errors. These factors include variations in reagent concentration (e.g., due to reagent stability or instrument pipetting errors), instrument processing steps (e.g., reagent dispense volumes, incomplete aspiration after wash steps resulting in reagent dilution, incubation timing), instrument conditions (detector temperature), and sample matrix effects (e.g. serum vs. plasma).

One method for verifying the amount or volume of a sample that is analyzed in an assay is described in U.S. Pat. No. 7,141,362. The method detects the amount of human blood coagulation Factor XIII (hFXIII) subunits a and b in a sample to determine the volume of a sample, and can also be used to distinguish plasma and serum from other types of biological samples. The amount of hFXIII in a sample is detected in an immunoassay using antibodies to hFXIII subunits immobilized on solid supports.

Further, replicate analysis of samples such as calibrators, controls or patient specimens (serum or plasma) can produce inconsistent results leading to high coefficients of variation (percent relative standard deviation). In some cases, the variation can be as high as 50% or more and can be sufficient to produce a response classified as positive for some replicates but negative for others. This variability is unacceptable for critical assays such as HIV detection. This invention addresses errors in analysis that lead to high coefficients of variation.

SUMMARY OF THE DISCLOSURE

The present disclosure describes a normalization factor that can be used as a normalization standard and/or internal control in a biological assay. In some embodiments, the normalization standard is attached to a solid support that is included in the assay. In one aspect, a method for normalizing results in an immunoassay for the detection of analytes in a biological sample is described. The analytes are detected by binding to binding members that specifically bind an individual analyte. By including a normalization factor in the assay, errors introduced by variations in sample processing or biological matrix effects associated with various sample types can be corrected. In some embodiments, the normalization factor does not specifically bind to an analyte in the sample.

Thus, in some embodiments, the biological sample is incubated with one or more binding members which bind one or more of the analytes in the sample, and detecting whether any of the analytes bind to the binding members. For example, if the analyte is an antigen, the corresponding binding member can be an antibody that specifically binds the antigen. Likewise, if the analyte is an antibody, the corresponding binding member can be an antigen that specifically binds the antibody. Thus, an individual target analyte specifically binds to a corresponding binding member, and a panel of analytes can bind to a corresponding panel of binding members. The analytes that bind to a given binding member are then identified. One means of such identification is to use binding members that are immobilized on a solid support, with a different solid support for each binding member. For example, molecules of only one binding member are immobilized on an individual solid support, and the solid supports for different binding members are distinguishable from each other by means other than the binding members themselves. The solid supports can be distinguished from each other by using differentiation parameters associated with the solid supports, all supports bearing any one binding member being differentiable from all supports bearing any of the other binding members by the differentiation parameters. Thus, the differentiation parameters can be used to divide the solid supports into subpopulations that are differentiable from each other.

The detection of immunological binding between analytes from the sample and the binding members can be achieved by the use of binding agents. For example, binding agents having binding affinity for the normalization factor and binding agents having binding affinity for each of the analytes in the sample can be used to detect binding. In certain embodiments, the binding agents are incubated with the solid supports having binding members immobilized thereon under conditions that promote binding of the binding agents to the normalization factor and the analytes. In some embodiments, the binding agent is conjugated to a label. In some embodiments, the label is biotin. In some embodiments, the label is a detectable label, such as a fluorescent moiety.

Following incubation of the binding agents with the solid supports, the solid supports are recovered to separate the supports having the analytes and/or normalization factor bound thereto from unbound binding agents. In embodiments where the binding agent is conjugated to biotin, the solid supports can be incubated with streptavidin that is coupled to a detectable label. In some embodiments, the detectable label is a fluorescent label, such as phycoerythrin (PE). The amount of label bound to the solid supports is then detected. For example, the label can be detected by any method capable of measuring the amount of fluorescent signal emitted by the label.

The amount of label detected can be correlated with the differentiation parameters to obtain values that are representative of the level or amount of each individual analyte in the sample, as well as values that are representative of the level or amount of the normalization factor that is bound to the solid support. This allows the values representative of the levels of each individual analyte in the sample to be normalized to the value representative of the level of the normalization factor. The normalization allows variations in sample processing to be corrected, thereby improving the performance of the assay. The normalization also allows for variations in signal intensity, for example, from the detectable label, to be corrected, where the variation in signal intensity is due to the source of the sample (i.e., biological matrix effects).

In one embodiment, the normalization factor is human Factor XIII (hFXIII). In one embodiment, the method uses human Factor XIII coupled to a solid support as a normalization factor and/or internal control in a biological assay. Thus, in certain embodiments, one subpopulation of solid supports has hFXIII immobilized thereon. In some embodiments, the solid support is a bead or magnetic bead. In one embodiment, hFXIII is immobilized to a bead. In some embodiments, hFXIII is immobilized to a magnetic bead. In one embodiment, hFXIII immobilized to a bead or magnetic bead is referred to as a Signal Normalization Bead (SNB). The hFXIII bound to the solid support can be detected using an anti-hFXIII antibody. The anti-hFXIII antibody is typically not present in the biological sample isolated from the subject, but is added with other binding agents specific for analytes during sample processing in order to provide a means for detecting the hFXIII immobilized on the solid support, as described herein.

In some embodiments, one subpopulation of solid supports has antibodies to hFXIII immobilized thereon, which are used to detect binding of hFXIII (i.e., subunits a and/or b) present in the biological sample, as described in U.S. Pat. No. 7,141,362, which is incorporated by reference herein in its entirety. Thus, in some embodiments, anti-hFXIII antibodies are immobilized on a solid support comprising a bead or magnetic bead. In one embodiment, the bead or magnetic bead having anti-hFXIII antibodies immobilized thereon is referred to as a Serum Verification Bead (SVB). The SVB allows for confirmation that a serum sample was present in the assay.

In another aspect, a method for normalizing assay results is provided, such as a multiplex immunoassay for the detection of analytes in a biological sample. In certain embodiments, the immunoassay is for the detection of a panel of analytes whose levels are indicative of infection with human immunodeficiency virus (HIV) in a biological sample. The panel of analytes are detected by binding to a corresponding set or panel of binding members that each individually bind an individual analyte. Binding of one or more analytes in the sample to one or more binding members indicates that the biological sample is from a subject infected with HIV. By including a normalization factor, errors introduced by variations in sample processing or variations due to biological matrix effects can be corrected.

In some embodiments, the members of the panel of analytes are HIV antigens and/or antibodies that bind to HIV-1 and HIV-2. In certain embodiments, the members of the panel of analytes include:
(i) p24 antigen,
(ii) antibodies to HIV Type 1,
(iii) antibodies to HIV Type 2,
(iv) antibodies to HIV Type 1, group O, and
(v) antibodies to HIV Type 1, group M.

In some embodiments, the binding member specifically binds to one member of the panel of HIV analytes described above. In some embodiments, the binding member is an anti-p24 antibody, HIV-1 envelope protein gp-160, SPOH, or AFR.

The immunoassay can also include a solid support having an antibody to human Factor XIII immobilized thereon. As described above, the antibody to human Factor XIII binds to hFXIII present in the biological sample, and thus serves as an assay to verify that the sample contained serum or plasma, helping to avoid false negative results. Thus, in one embodiment, the binding member is an antibody to human Factor XIII.

The binding of the panel of analytes whose levels are indicative of infection with HIV can be detected using biotinylated conjugates. In some embodiments, the biotinylated conjugates bind to HIV antigens, antibodies to HIV-1, and antibodies to HIV-2. In some embodiments, the biotinylated conjugates bind to a normalization factor. In some embodiments, the normalization factor is hFXIII.

In some embodiments, the biotinylated conjugates are selected from 39-PFN-BgG, SV2V, AFR, antibodies to p24 antigen, and antibodies to human Factor XIII In some embodiments, the solid support is a bead or a magnetic bead.

In some embodiments, the solid support is coupled to tetramethylcadaverine rhodamine (TMRC).

The invention further resides in a kit that includes a normalization factor immobilized on a solid support, and a panel of binding members, each of which is immobilized on a solid support. The panel of binding members includes any of the various binding members presented above, and the solid supports further contain differentiation parameters that are selected such that all of the supports bearing any one binding member of the panel are differentiable by these parameters from all of the supports bearing other binding members of the panel.

In some embodiments, the kit includes a panel of binding members for determining whether a subject is infected with HIV or for determining the stage of infection in the subject. In some embodiments, the subject is a human.

In certain embodiments, the kit further provides tetramethylcadaverine rhodamine (TMRC) immobilized on a solid support.

DEFINITIONS

A "binding agent" is a compound having binding affinity for another compound. For example the binding agent can bind with high affinity to the normalization factor that is immobilized on a solid support. The binding agent can also bind to an analyte in the biological sample. The binding agent can be immunoreactive with the normalization factor or a target analyte. For example, the binding agent can be an antibody that specifically binds the normalization factor or an antigen in the biological sample, or the binding agent can be an antigen that specifically binds an antibody in the biological sample. The binding agent can be conjugated to a label that allows the binding agent to be detected. In some embodiments, the binding agent is not immobilized on a solid support.

The term "binding member" is used herein to denote a molecule or agent that specifically binds to a target analyte. The binding member can be immunoreactive with a target analyte. For example, the binding member can be an antigen that specifically binds to an antibody in the biological sample, or the binding member can be an antibody that specifically binds to an antigen in the biological sample. The binding member can be immobilized on a solid support, including but not limited to a bead or magnetic bead.

A "normalization factor" is a molecule that can be used to normalize an assay result. The normalization factor typically does not react with or bind with high affinity to an analyte of interest in the sample.

The term "label" or "detectable moiety" is used herein to denote a composition detectable by spectroscopic, photochemical, biochemical, immunochemical, chemical, or other physical means. Examples of labels are 32P, fluorescent dyes, electron-dense reagents, enzymes (e.g., as commonly used in an ELISA), biotin, digoxigenin, and haptens and proteins or other entities which can be made detectable, e.g., by incorporating a radiolabel into the peptide or by being used to detect antibodies specifically reactive with the peptide. The labels can be incorporated, for example, into antibodies and/or other proteins at any position. Any method known in the art for conjugating the antibody or protein (peptide) to the label can be employed, for example, using methods described in Hermanson, *Bioconjugate Techniques* 1996, Academic Press, Inc., San Diego. Alternatively, methods using high affinity interactions can achieve the same results where one of a pair of binding partners binds to the other, e.g., biotin and streptavidin. The proteins of the invention as described herein can be directly labeled as with isotopes, chromophores, lumiphores, chromogens, or indirectly labeled such as with biotin to which streptavidin in a complex with a fluorescent, radioactive, or other moiety that can be directly detected can then bind. Thus, a biotinylated antibody is considered a "labeled antibody" as used herein.

The term "antibody" as used herein refers to a polypeptide encoded by an immunoglobulin gene or immunoglobulin genes, or fragments thereof, which specifically bind and recognize an analyte (antigen). The recognized immunoglobulin light chains are classified as either kappa or lambda. Immunoglobulin heavy chains are classified as gamma, mu, alpha, delta, or epsilon, which in turn define the immunoglobulin classes, IgG, IgM, IgA, IgD and IgE, respectively.

An example of a structural unit of immunoglobulin G (IgG antibody) is a tetramer. Each such tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains, respectively.

Antibodies exist as intact immunoglobulins or as well-characterized fragments produced by digestion of intact immunoglobulins with various peptidases. Thus, for example, pepsin digests an antibody near the disulfide linkages in the hinge region to produce F(ab')2, a dimer of Fab which itself is a light chain joined to VH-CH1 by a disulfide bond. The F(ab')2 dimer can be reduced under mild conditions to break the disulfide linkage in the hinge region, thereby converting the F(ab')2 dimer into two Fab' monomers. The Fab' monomer is essentially an Fab with part of the hinge region (see, Paul (Ed.) Fundamental Immunology, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or by de novo synthesis using recombinant DNA methodologies such as single chain Fv.

The expression "specifically (or selectively)" in reference to binding to an antibody, or "specifically (or selectively) immunoreactive with" or "having binding specificity for," when referring to a protein, peptide, or antigen, refers to a binding reaction which is determinative of the presence of the protein, peptide, or antigen in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein can be selected to obtain antibodies specifically immunoreactive with that protein and not with other proteins. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane Antibodies, A Laboratory Manual, Cold Spring Harbor Publications, NY (1988) for a description of immunoassay formats and conditions that can be used to determine specific immunoreactivity. Typically, a specific or selective reaction will be at least twice the background signal or noise, and more typically more than 10 to 100 times background.

Antibodies for use in certain embodiments of the present invention are anti-human antibodies, particularly those anti-human antibodies that are labeled. Preferred among these anti-human antibodies are those that are antibodies to human IgG, those that are antibodies to human IgM, and those that are antibodies to human IgA.

The term "biological sample" encompasses a variety of sample types obtained from an organism. The term encompasses bodily fluids such as blood, saliva, serum, plasma, urine and other liquid samples of biological origin, solid tissue samples, such as a biopsy specimen or tissue cultures or cells derived therefrom and the progeny thereof. As described herein, typically, the biological sample will be a bodily fluid or tissue that contains detectable amounts of an analyte of interest, e.g., an antigen, antibody, protein, peptide, nucleic acid, or small molecule. The term encompasses samples that have been manipulated in any way after their procurement, such as by treatment with reagents, solubilization, sedimentation, or enrichment for certain components. The term encompasses a clinical sample, and also includes cells in cell culture, cell supernatants, cell lysates, serum, plasma, other biological fluids, and tissue samples. Preferred biological samples are blood samples, plasma samples, and serum samples.

The term "solid support" is used herein to denote a solid inert surface or body to which an agent, such as an antibody or an antigen, that is reactive in any of the binding reactions described herein can be immobilized. The term "immobilized" as used herein denotes a molecularly based coupling that is not dislodged or de-coupled under any of the conditions imposed during any of the steps of the assays described herein. Such immobilization can be achieved through a covalent bond, an ionic bond, an affinity-type bond, or any other chemical bond.

The term "particles" is used herein to denote solid bodies, often with linear dimensions on the micron scale (i.e., less than 100 microns), of any shape or surface texture. The term "beads" is used herein to denote particles that are spherical or near-spherical in shape, often polymeric in composition.

"Multiplex" assays are analyses that simultaneously measure the levels of more than one analyte in a single sample.

The term "analyte" or "target analyte" is used herein to denote a molecule that is present in a biological sample and is indicative of the presence or absence of a biological condition in a subject, such as a human subject. The term biological condition is used without limitation, and can include both normal and abnormal conditions. For example, the biological condition can be a pathological condition such as a disease, infection, cancer, or autoimmune disorder. The analyte can also indicate the state or progression of a disease or infection, such as during treatment of the disease or during different stages of an infection. The analyte can also indicate a diagnosis or prognosis of a biological condition.

The term "labeled binding moiety" refers to a molecule or reagent that is conjugated or coupled to a label. The label can be a detectable label, such as a fluorophore, or can be indirectly labeled such as with biotin or streptavidin, or with an enzyme that is useful for producing a detectable signal, such as alkaline phosphatase (AP) or horse radish peroxidase (HRP). The labeled binding moiety can bind to a binding agent or, where the label is avidin, streptavidin or an equivalent, to a biotinylated conjugate.

The term "differentiation parameter" is used herein to denote a characteristic of the solid support that is independent of the binding member that is attached or immobilized to the solid support. Thus, a differentiation parameter allows solid supports with different binding members immobilized thereon to be distinguished from each other by means other than the binding members themselves.

The term "biological matrix" refers to the source of the sample that contains the analytes of interest. For example, the biological matrix can be a biological fluid such as, but not limited to, serum, plasma, whole blood, urine, saliva, lymph, or cerebral spinal fluid. The term "biological matrix effect" refers to the variation in the assay signal when the sample is derived from different biological matrices.

DESCRIPTION OF SELECTED EMBODIMENTS

Figure 1:
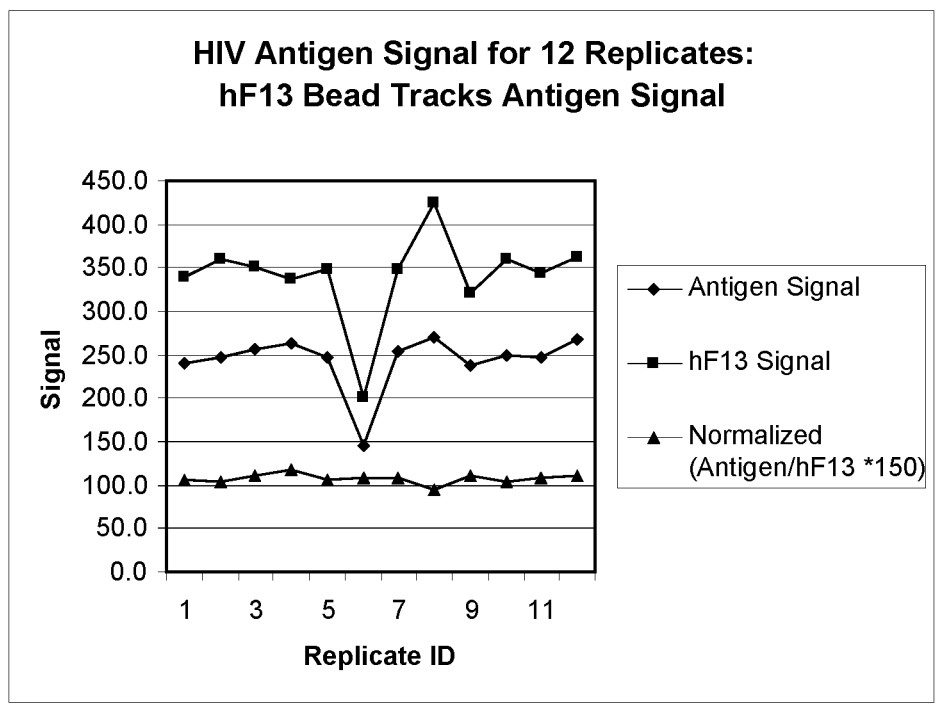
FIG. 1 illustrates the use of a human Factor XIII coated bead as a control and to produce a normalized signal in a representative HIV assay that detects HIV p24 antigen. Twelve (12) replicates were performed, and the data was normalized as described in Example 1.

The present disclosure provides compositions and methods for correcting for variations in sample processing and/or biological matrix effects when performing biological assays. The composition comprises a normalization factor coupled to a solid support. In some embodiments, the normalization factor can be any suitable molecule that is capable of being attached to a solid support and that does not specifically bind to a target analyte in the biological sample. The normalization factor can be covalently or non-covalently attached to the solid support. In some embodiments, the solid support is a bead or magnetic bead. Thus, in some embodiments, the normalization factor is coupled to a bead, and the normalization bead interacts with reagents used during subsequent detection steps of the assay in the same manner as the beads that specifically bind analytes from the sample. The solid support coupled to a normalization factor can be used to verify correct sample processing and for assay signal normalization. Signal normalization provides for improved assay precision for biological samples, controls, and calibrators, and improves signal stability over the lifetime of reagents used in the assay.

In one embodiment, the normalization factor is human Factor XIII (hFXIII). In one embodiment, the method uses human Factor XIII coupled to a solid support as a normalization factor and/or internal control in a biological assay. In one aspect, a solid support coupled to hFXIII is provided for use as a normalization standard and/or internal control.

Thus, in some embodiments, the hFXIII-coupled solid support can be used in immunoassays to correct for variations in sample processing. In one embodiment, the hFXIII-coupled solid support allows normalizing the amount of signal detected to improve the precision of the assay. The signal can be produced, for example, by a label. In one embodiment, the hFXIII-coupled solid support allows normalizing the amount of label detected in order to correct for loss of the amount of detectable label during storage of the reagents used in the method.

In some embodiments, the hFXIII-coupled solid support allows detecting an invalid assay, for example, by detecting when the assay signal falls below a preset limit. For example, the signal for each sample can be normalized using hFXIII, and the normalized signal compared to expected control values. If the normalized sample signal is too low, then the assay results may be compromised due to matrix effects or other processing error, and the results can be flagged as invalid.

The normalization factor coupled to a solid support can be used in a method for analyzing a biological sample for the presence of one or more analytes whose levels are indicative of a disease state in a subject. In some embodiments, the one or more analytes comprise a panel of analytes. Analytes of the present disclosure include antigens and antibodies that are present in a biological sample from a subject, including but not limited to a human subject. In some embodiments, the presence, absence or the level of an analyte in a sample indicates that the subject suffers from or is at risk of developing a disease or other pathological condition. For example, in some embodiments, the analytes indicate that the subject is infected with a virus, such as a retrovirus. Thus, in some embodiments, the analytes indicate that the subject is infected with human immunodeficiency virus (HIV), hepatitis C virus (HCV), or herpes simplex virus (HSV). In one embodiment, the analytes indicate that the subject is infected with HIV. Analytes that are indicative of HIV infection of a human subject include HIV antigens such as p24 antigen, antibodies to HIV-1 (groups M, O, N and P), and antibodies to HIV-2 (including numerous subtypes).

In some embodiments of the method, a biological sample is incubated with a plurality of solid supports having binding members immobilized thereon for each analyte in the panel. Binding members of the present disclosure include antigens and antibodies that are capable of specifically binding to an analyte in the biological sample. For example, binding members that are capable of specifically binding to analytes indicative of HIV infection of a human subject include anti-p24 antibodies, gp160 protein for detection of HIV-1, 39 PFN for detection of HIV-1/M, AFR for detection of HIV-1/O, SPOH for detection of HIV-2, gp36 peptide for detection of HIV-2, and SV2V for detection of HIV-2. 39 PFN and AFR are peptides that mimic the immunodominant regions of HIV-1 groups M and O, respectively. SPOH and SV2V are peptides that mimic the immunodominant regions of HIV-2. The sequences of the peptides are provided in the following table (Table 1).

TABLE 1

Sequences of peptides that bind HIV antibodies.

| HIV Peptides Reactivity | Basic HIV-1/M | Cysteine HIV-1/O | HIV-1/O | HIV-2 | HIV-2 |
|---|---|---|---|---|---|
| Peptide | 39PFN | Biotinyl-AFR21 | AFR21K | Biotinyl-SV2VPFVN | 41SPOH |
| PN | 4052076 | 4055465 | 701073 | 4055461 | 960453 |
| #Amino Acids | 33 | 22 | 24 | 28 | 26 |
| MW | 3704.4 | 2763.3 | 2793.3 | 3507.0 | 3054.5 |
|  | SEQ ID NO: 1 | SEQ ID NO: 2 | SEQ ID NO: 3 | SEQ ID NO: 4 | SEQ ID NO: 5 |
| Sequence | R Arginine |  |  |  | R Arginine |
|  | I Isoleucine |  |  |  | V Valine |
|  | L Leucine |  |  |  | T Threonine |
|  | A Alanine |  |  |  | A Alanine |
|  | V Valine |  |  |  | I Isoleucine |
|  | E Glutamic Acid |  |  | Biotinyl | E Glutamic Acid |
|  | R Arginine |  | K Lysine | K Lysine | K Lysine |
|  | Y Tyrosine | Biotinyl | K Lysine | Y Tyrosine | Y Tyrosine |
|  | L Leucine | L Leucine | L Leucine | L Leucine | L Leucine |
|  | K Lysine | N Asparagine | N Asparagine | Q Glutamine | Q Glutamine |
|  | D Aspartic Acid | Q Glutamine | Q Glutamine | D Aspartic Acid | D Aspartic Acid |
|  | Q Glutamine | Q Glutamine | Q Glutamine | Q Glutamine | Q Glutamine |
|  | Q Glutamine | R Arginine | R Arginine | A Alanine | A Alanine |
|  | L Leucine | L Leucine | L Leucine | R Arginine | R Arginine |
|  | L Leucine | L Leucine | L Leucine | L Leucine | L Leucine |
|  | G Glycine | N Asparagine | N Asparagine | N Asparagine | N Asparagine |
|  | I Isoleucine | S Serine | S Serine | S Serine | S Serine |
|  | W Tryptophan | W Tryptophan | W Tryptophan | W Tryptophan | W Tryptophan |
|  | G Glycine | G Glycine | G Glycine | G Glycine | G Glycine |
|  | C Cysteine | C Cysteine | C Cysteine | C Cysteine | C Cysteine |
|  | S Serine | K Lysine | K Lysine | A Alanine | A Alanine |
|  | G Glycine | G Glycine | G Glycine | F Phenalanine | F Phenalanine |
|  | K Lysine | R Arginine | R Arginine | R Arginine | R Arginine |
|  | L Leucine | L Leucine | L Leucine | Q Glutamine | Q Glutamine |
|  | I Isoleucine | V Valine | V Valine | V Valine | V Valine |
|  | C Cysteine | C Cysteine | C Cysteine | C Cysteine | C Cysteine |
|  | T Threonine | Y Tyrosine | Y Tyrosine | H Histidine |  |
|  | T Threonine | T Threonine | T Threonine | T Threonine |  |
|  | A Alanine | S Serine | S Serine | T Threonine |  |
|  | V Valine | V Valine | V Valine | V Valine |  |
|  | P Proline |  |  | P Proline |  |
|  | F Phenalanine |  |  | F Phenalanine |  |
|  | N Asparagine |  |  | V Valine |  |
|  |  |  |  | N Asparagine |  |

In some embodiments, the binding member is conjugated to another protein, such as BSA, which is attached to a solid support. In one embodiment, the binding member is an anti-hFXIII antibody. Thus, in one embodiment, the biological sample is incubated with a plurality of solid supports having an anti-hFXIII antibody immobilized thereon. The incubation is performed under conditions that promote binding of each analyte, if present in the sample, to the binding members immobilized on the solid supports. Conditions that promote binding of the analytes to the binding members on the solid support include incubating the sample with the solid supports in a buffered solution such as phosphate buffer at a pH of about 7.0 to about 7.4, at a temperature of about 25-37 degrees C. for about 10 to 60 minutes. In some embodiments, the binding constitutes immunological binding.

The determination that immunological binding has occurred constitutes one or more steps in certain embodiments of this invention, and this can involve the separation or recovery of antigen-antibody complexes from unbound antigen or antibody. One means of achieving such separation or recovery is by the use of solid supports. Thus, the present disclosure further provides a plurality of solid supports having binding members immobilize thereon for each analyte of the panel of analytes. In some embodiments, the plurality of solid supports are divided into subpopulations characterized in that each subpopulation comprises a binding member that binds to only one analyte of the panel of analytes. In some embodiments, each subpopulation of solid supports is differentiable from the other subpopulations of solid supports by a differentiation parameter, as described herein.

In certain embodiments, there is provided a subpopulation of solid supports having human Factor XIII immobilized thereon. In some embodiments, hFXIII is immobilized to a bead or magnetic bead. In one embodiment, hFXIII immobilized to a bead or magnetic bead is referred to as a Signal Normalization Bead (SNB).

In certain embodiments, a subpopulation of solid supports has an antibody that binds hFXIII immobilized thereon. In some embodiments, the anti-hFXIII antibody is immobilized to a bead or magnetic bead. In one embodiment, anti-hFXIII antibody immobilized to a bead or magnetic bead is referred to as a Serum Verification Bead (SVB). As described herein, the SVB can be used to verify the amount of biological sample added to the assay, and whether the sample was from serum, plasma, or some other biological sample.

I. Solid Supports

Any type of solid support can be used in the invention. The solid support can comprise any surface capable of binding a protein, being exposed to a sample, and separated into discrete populations. The solid support can be the wall or floor of an assay vessel, or a dipstick or other implement to be inserted into an assay vessel, or particles placed inside or suspended in an assay vessel. Particles, and especially beads, are particularly useful in many embodiments, including beads that are microscopic in size (i.e., microparticles) and formed of a polymeric material. Polymers useful as microparticles are those that are chemically inert relative to the components of the biological sample and to the assay reagents other than the binding members that are immobilized on the microparticle surface. Preferred microparticle materials, particularly when fluorescent labels are used in the assay, are those with minimal autofluorescence, and that are solid and insoluble in the sample and in any buffers, solvents, carriers, diluents, or suspending agents used in the assay, in addition to allowing immobilization of the assay reagent. Examples of suitable polymers are polystyrenes, polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle. The size range of the microparticles can vary. In some embodiments, the microparticles range in diameter from about 0.3 micrometers to about 100 micrometers, and other embodiments, from about 0.5 micrometers to about 40 micrometers, and in still other embodiments, from about 2 micrometers to about 10 micrometers.

In embodiments where the solid support is a bead, the biological sample can be incubated with from about 0.1 µg to about 2.0 µg (microgram) of beads per sample in a reaction vessel. For example, the sample can be incubated with about 0.1 to about 2.0 µg, about 0.3 to about 1.7 µg, about 0.5 to about 1.5 µg, about 0.7 to about 1.2 µg, or about 0.8 to about 1.0 µg of beads. In some embodiments, the amount of beads incubated with the sample is sufficient to produce a concentration of about 0.002 micrograms/microliter (µg/µL) to about 0.04 µg/µL in a reaction volume of about 50 µL. For example, the concentration can range from about 0.002 to about 0.040 µg/µL, about 0.004 to about 0.035 µg/µL, about 0.008 to about 0.030 µg/µL, about 0.010 to about 0.025 µg/µL, about 0.010 to about 0.020 µg/µL, or about 0.012 to about 0.018 µg/µL. Higher bead concentrations reduce the time to count the minimum number of beads (e.g., 50-100 bead events) required to determine the median signal for a given reaction vessel. In some embodiments, 200 bead events are counted per reaction sample.

In some embodiments, the method further comprises recovering the solid supports from the incubated sample described above. Particle recovery and washing can be facilitated by the use of particles that are formed of or contain a magnetically responsive material, i.e., any material that responds to a magnetic field. Separation of the solid and liquid phases, either after incubation or after a washing step, is then achieved by imposing a magnetic field on the reaction vessel in which the particles and sample are incubated, causing the particles to adhere to the wall of the vessel and thereby permitting the liquid to be removed by decantation or aspiration. Magnetically responsive materials of interest in this invention include paramagnetic materials, ferromagnetic materials, ferrimagnetic materials, and metamagnetic materials. Examples, include, e.g., iron, nickel, and cobalt, as well as metal oxides such as $Fe_3O_4$, $BaFe_{12}O_{19}$, CoO, NiO, $Mn_2O_3$, $Cr_2O_3$, and CoMnP.

Methods of, and instrumentation for, applying and removing a magnetic field as part of an assay are known to those skilled in the art and reported in the literature. Examples of literature reports are Forrest et al., U.S. Pat. No. 4,141,687 (Technicon Instruments Corporation, Feb. 27, 1979); Ithakissios, U.S. Pat. No. 4,115,534 (Minnesota Mining and Manufacturing Company, Sep. 19, 1978); Vlieger, A. M., et al., *Analytical Biochemistry* 205:1-7 (1992); Dudley, *Journal of Clinical Immunoassay* 14:77-82 (1991); and Smart, *Journal of Clinical Immunoassay* 15:246-251 (1992).

Magnetically responsive material can be dispersed throughout the polymer, applied as a coating on the polymer surface or as one of two or more coatings on the surface, or incorporated or affixed in any other manner that secures the material in to the particle. The quantity of magnetically responsive material in the particle is not critical and can vary over a wide range. The quantity can affect the density of the microparticle, however, and both the quantity and the particle size can affect the ease of maintaining the microparticle in suspension for purposes of achieving maximal contact between the liquid and solid phase and for facilitating flow cytometry. An excessive quantity of magnetically responsive material in the microparticles may produce autofluorescence at a level high enough to interfere with the assay results. Therefore, in some embodiments, the concentration of magnetically responsive material is low enough to minimize any autofluorescence emanating from the material. With these considerations in mind, the magnetically responsive material in a particle in accordance with this invention is, for example, from about 0.05% to about 75% by weight of the particle as a whole. In some embodiments, the weight percent range is from about 1% to about 50%, e.g., from about 2% to about 25%, e.g., from about 2% to about 8%.

In some embodiments, the binding members are covalently coupled to the solid support. In some embodiments, the binding member is an antibody to hFXIII, which is covalently linked to the solid support. In some embodiments, the binding members are proteins that are covalently coupled to the solid support using carbodiimide-mediated coupling chemistry. Other methods of covalently coupling proteins to a solid support are well known in the art. For example, proteins can be coupled to a reactive carboxy group on polystyrene beads. The initial carboxy bead can be chemically converted to amino or activated carbon-carbon double groups. Solid supports can also contain reactive chloroalkyl groups or similar alkylating agents which are capable of reacting directly with protein amino residues.

In other embodiments, the binding members are non-covalently coupled to the solid support. For example, the proteins can be adsorbed to the surface of the solid support via electrostatic interactions. In some embodiments, the solid support can be coated with streptavidin in order to capture biotinylated proteins, antigens and antibodies using the strong avidity of streptavidin for biotin. The streptavidin can be covalently coupled to the solid support using conventional carbodiimide activation chemistry. Other binding proteins such as Protein G or A can be used to immobilize antibodies on beads.

In some embodiments, the normalization factor is covalently coupled to the solid support. In some embodiments, the normalization factor is hFXIII, which is covalently linked to a solid support. For example, hFXIII can be covalently linked to a bead using carbodiimide mediated coupling chemistry. In one embodiment, hFXIII is coupled to a unique bead region. In some embodiments, hFXIII is non-covalently coupled to the solid support, for example, by adsorption. In some embodiments, hFXIII is indirectly coupled to the solid support, for example, by first covalently coupling an antibody to hFXIII to the solid support, and then incubating the solid support with hFXIII to produce an immunocoupled hFXIII solid support.

In some embodiments, the assay includes a solid support coupled to an anti-human Factor XIII antibody. In one embodiment, the anti-human Factor XIII antibody is coupled to a bead. In one embodiment, the bead is coupled to a mouse anti-human FXIII monoclonal antibody. This embodiment is referred to as a Serum Verification Bead (SVB). The SVB is useful to detect native human Factor XIII in the sample to verify sample addition. Examples of beads coupled to anti-human Factor XIII monoclonal antibodies are described in U.S. Pat. No. 7,141,362, which is incorporated in its entirety by reference herein.

After the solid supports are recovered from the biological sample, for example, by using the methods described above, the solid supports are incubated with reagents having binding affinity for each of the analytes and reagents having binding affinity for hFXIII In some embodiments, the reagents are biotinylated conjugates. In some embodiments, the biotinylated conjugates are biotinylated proteins, peptides, or antibodies. Examples of biotinylated conjugates include: 39-PFN-BgG-Biotin for detection of HIV-1/M antibodies; SV2V-biotin for detection of HIV-2 antibodies; AFR-biotin for detection of HIV-1/O antibodies; and biotinylated anti-p24 antibodies for detection of p24 antigen. In some embodiments, the biotinylated conjugate is a biotinylated antibody that binds to human FXIII.

Methods of biotinylating peptides are well known in the art. For example, the most common and versatile method for biotinylation is by reaction of biotin derivatives possessing the N-hydroxysuccinimide ester group. This chemical functionality allows the formation of stable covalent amide bonds between biotin and the protein amino group under very mild reaction conditions (room temperature, neutral to high pH) usually within a short period of time (about 1 hour) to completion. Biotin derivatives are commercially available and the distance and linkage type between biotin and protein can be tailored to the need of the specific target biotin conjugate. Biotin derivatives which contain active hydrazide groups can also be used to link biotin to available carbonyl moieties of proteins. These compounds are often used if there is a need to directly label the protein near its sugar containing domains. Biotin derivatives which carry N-ethylmaleimide groups or similar unsaturated carbon-carbon bonds are used to target protein thiols and provide another example for site specific labeling of proteins. Other more specialized biotin derivatives carry chemical functionalities such as aryl azides which can be activated photochemically using ultraviolet light. Once photochemically activated, these transient biotin species are allowed to react with various types of protein residues. See, for example, Richard P. Haugland, Handbook of Fluorescent Probes and Research Chemicals, Chapter 4, Biotins and Haptens, pp, 63-80, Sixth Edition, 1996, which is incorporated by reference herein.

The biotinylated conjugates are incubated under conditions which promote the binding of the biotinylated conjugates to hFXIII and the analytes. Suitable conditions include phosphate buffer with NaCl, protein stabilizers, blockers, and preservatives. The pH can be in the range of about 7.0-7.4.

In some embodiments, after the solid supports are incubated with the biotinylated conjugates, excess conjugate is removed by washing and the solid supports are incubated with a labeled binding moiety. In some embodiments, the labeled binding moiety is selected from streptavidin and avidin. In some embodiments, the labels are fluorophores, many of which are reported in the literature and thus known to those skilled in the art, and many of which are readily available from commercial suppliers to the biotechnology industry. Literature sources for fluorophores include Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I., *Ann. Rev. Biochem.*, 40: 83-114 (1971); Stryer, L., *Ann. Rev. Biochem.* 47: 819-846 (1978); Wang et al., *Tetrahedron Letters* 31: 6493-6496 (1990); and Wang et al., *Anal. Chem.* 67: 1197-1203 (1995).

The following are examples of fluorophores that can be used as labels:

4-acetamido-4'-isothiocyanatostilbene-2,2'disulfonic acid acridine acridine isothiocyanate 5-(2'-aminoethyl)aminonaphthalene-1-sulfonic acid (EDANS)

4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin
7-amino-4-methylcoumarin (AMC, Coumarin 120)
7-amino-4-trifluoromethylcoumarin (Coumaran 151)
cyanine dyes
cyanosine
4',6-diaminidino-2-phenylindole (DAPI)
5',5"-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin
eosin isothiocyanate
erythrosin B
erythrosin isothiocyanate
ethidium
5-carboxyfluorescein (FAM)
5-(4,6-dichlorotriazin-2-yl)aminofluorescein (DTAF)
2',7'-dimethoxy-4'5'-dichloro-6-carboxyfluorescein (JOE)
fluorescein
fluorescein isothiocyanate
fluorescamine
IR144
IR1446
Malachite Green isothiocyanate
4-methylumbelliferone
ortho cresolphthalein
nitrotyrosine
pararosaniline
Phenol Red
phycoerythrin (including but not limited to B and R types)
o-phthaldialdehyde
pyrene
pyrene butyrate
succinimidyl 1-pyrene butyrate
quantum dots
Reactive Red 4 (Cibacron☐ Brilliant Red 3B-A)
6-carboxy-X-rhodamine (ROX)
6-carboxyrhodamine (R6G)
lissamine rhodamine B sulfonyl chloride rhodamine
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
lanthanide chelate derivatives A prominent group of fluorophores for immunoassays are fluorescein, fluorescein isothiocyanate, phycoerythrin, rhodamine B, and Texas Red (sulfonyl chloride derivative of sulforhodamine 101). Phycoerythrin is particularly prominent. Thus, in one embodiment, the labeled binding moiety is streptavidin conjugated with phycoerythrin (PE). Any of the fluorophores in the list preceding this paragraph can be attached to binding members by conventional covalent bonding, using appropriate functional groups on the fluorophores and on the binding moieties. The recognition of such groups and the reactions to form the linkages will be readily apparent to those skilled in the art.

Other labels that can be used in place of the fluorophores are radioactive labels and enzyme labels. These are likewise known in the art.

After the solid supports are incubated with the labeled binding member, the solid supports are recovered using the recovery methods described above, and the amount of label that is bound to the supports is detected. In some embodiments, the detecting step is accomplished by measuring the amount of fluorescence signal produced by the fluorescent labels described above.

In some embodiments, the fluorescence signal is detected by flow cytometry. Flow cytometry is used for bead size classification (forward/side scatter) with a dual laser system to classify bead dyed regions and then quantitate the fluorescent signal from each region. Other multiplex methods for identification of solid phase populations and the associated population signal are known to those of skill in the art. Examples include Luminex Magpix® technology using stop-flow immobilization of beads followed by identification and quantitation using LED-CCD imaging (see the internet at luminexcorp.com/Products/Instruments/MAG-PIX/). Another example is Ilumina Veracode™ multiplex technology which uses cylindrical glass microbeads having high-density codes as the solid phase and a groove plate detection method (see the internet at illumina.com/systems/beadxpress/technology.ilmn). Other examples of multiplex technology include chip based assays such as Randox Bio-Chip Array Technology assays (see the internet at randox.com/Biochip%20Immunoassays.php).

In some embodiments, the fluorescent signal is generated using Lanthanide chelate reagents and is detected using time-resolved fluorescence. Lanthanide chelates are unique in that their fluorescence decays exhibit longer lifetimes and larger "Stoke's Shifts". The use of Lanthanide chelates allows higher sensitivities for immunoassay analyte detection. The chelates can be custom synthesized and linked to proteins and antibodies via analogous chemical conjugation techniques for conventional fluorophores like Fluorescein, Rhodamine, Phycoerythrin and others. The metal associated with the chelate that is most commonly used is Europium. A commercial system based on this technology is the DEL-FIA® (Dissociation-Enhanced Lanthanide Fluorescent Immunoassay) TRF (time resolved fluorescence) assay system (Perkin Elmer, Waltham. Mass.).

In some embodiments, the amount of label detected is correlated with the differentiation parameters described herein to obtain values that are individually representative of the levels of the analytes in the biological sample. In some embodiments, the values representative of the levels of the analytes are normalized to the values representative of the levels of the normalization factor. For example, in some embodiments, the values are normalized by dividing the value representative of the level of the analyte by the value representative of the level of the normalization factor (e.g., the ratio of the analyte signal/human FXIII signal), and multiplying the result by a constant to produce a normalized value. The normalized value (also referred to as the normalized signal) can be used to correct for variations in sample processing and biological matrix effects during performance of the method. In some embodiments, the normalized values significantly reduce the coefficient of variation (percent relative standard deviation) between different replicate assays using the same biological sample.

Signal normalization provides improved assay precision for samples, controls and calibrators used in the methods. Signal normalization also provides improved signal stability over the lifetime of the reagents used in the methods. It will be understood that the normalization factor can also be used to normalize values in assays for detecting other biological conditions in a subject, such as viral infections in addition to HIV, and/or other pathological conditions, such as acute or chronic disease.

II. Functional Groups

Coating of the particle surface with the appropriate assay reagent can be achieved by electrostatic attraction, specific affinity interaction, hydrophobic interaction, or covalent bonding. The polymer can be derivatized with functional groups for covalent attachment of the assay reagents by conventional means, notably by the use of monomers that contain the functional groups, such monomers serving either as the sole monomer or as a co-monomer. Examples of suitable functional groups are amine groups (—$NH_2$), ammonium groups (—$NH_3^+$ or —$NR_3^+$), hydroxyl groups (—OH), carboxylic acid groups (—COOH), and isocyanate groups (—NCO). Useful monomers for introducing carboxylic acid groups into polyolefins, for example, are acrylic acid and methacrylic acid.

Linking groups can be used as a means of increasing the density of reactive groups on the particle surface and also as a means of decreasing steric hindrance. Linking groups can also be used as a means of securing coating materials to the particle surfaces. Certain linking groups are monofunctional linkers comprising a reactive group as well as multifunctional crosslinkers comprising two or more reactive groups capable of forming a bond with two or more different functional targets (e.g., peptides, proteins, macromolecules, semiconductor nanocrystals, or substrate). In some embodiments, the multifunctional crosslinkers are heterobifunctional crosslinkers comprising two different reactive groups. Examples of suitable reactive groups are thiol (—SH), carboxylate (—COOR), carboxyl (—COOH), carbonyl (—C(O)—), amine ($NH_2$), hydroxyl (—OH), aldehyde (—CHO), hydroxyl (—OH), active hydrogen, ester, phosphate (—$PO_3$), and photoreactive moieties. Examples of amine reactive groups are isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Examples of thiol-reactive groups are haloacetyl and alkyl halide derivates, maleimides, aziridines, acryloyl derivatives, arylating agents, and thiol-disulfides exchange reagents. Examples of carboxylate reactive groups are diazoalkanes and diazoacetyl compounds, such as carbonyldiimidazoles and carbodiimides. Examples of hydroxyl reactive groups are epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Examples of aldehyde and ketone reactive groups are hydrazine derivatives for Schiff base formation or reduction amination. Examples of active hydrogen reactive groups are diazonium derivatives for Mannich condensation and iodination reactions. Examples of photoreactive groups are aryl azides and halogenated aryl azides, benzophenones, diazo compounds, and diazirine derivatives.

Other suitable reactive groups and classes of reactions useful in practicing the present invention are generally those that are well known in the art of bioconjugate chemistry. Currently favored classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, *Advanced Organic Chemistry*, 3rd Ed., John Wiley & Sons, New York, 1985; Hermanson, *Bioconjugate Techniques*, Academic Press, San Diego, 1996; and Feeney et al., *Modification Of Proteins*; Advances in Chemistry Series, Vol. 198, American Chemical Society, Washington, D.C., 1982.

In some embodiments, the functional group is a heterobifunctional crosslinker comprising two different reactive groups that contain heterocyclic rings that can interact with peptides and proteins. For example, heterobifunctional crosslinkers such as N-[γ-maleimidobutyryloxy]succinimide ester (GMBS) or succinimidyl 4[N-maleimidomethyl]cyclohexane-1-carboxylate (SMCC) comprise an amine reactive group and a thiol-reactive group that can interact with amino and thiol groups within peptides or proteins. Additional combinations of reactive groups suitable for heterobifunctional crosslinkers include, for example, carbonyl and sulfhydryl reactive groups; amine and photoreactive groups; sulfhydryl and photoreactive groups; carbonyl and photoreactive groups; carboxylate and photoreactive groups; and arginine and photoreactive groups. Examples of suitable useful linking groups are polylysine, polyaspartic acid, polyglutamic acid and polyarginine. N-hydroxysuccinimide (NHS), CMC 1-cyclohexyl-3-(2-morpholinoethyl)carbodiimide (CMC), N-Hydroxybenzotriazole (HOBt), and/or other crosslinking agents may be used.

Particles formed by conventional emulsion polymerization techniques from a wide variety of starting monomers are favorable in many cases since they exhibit at most a low level of autofluorescence. Conversely, particles that have been modified to increase their porosity and hence their surface area, i.e., those particles that are referred to in the literature as "macroporous" particles, tend to exhibit high autofluorescence and are often less desirable. Autofluorescence increases with increasing size and increasing amounts of divinylbenzene monomer.

Multiplexing, i.e., the performance of simultaneous assays for all analytes in a given panel, can be performed with the use of solid supports by utilization of differentiation parameters, as mentioned above and described below.

III. Differentiation Parameters

One example of a differentiation parameter is the particle diameter, where the solid supports are particles divided into groups with nonoverlapping diameter subranges. The widths of the diameter subranges and the spacing between mean diameters of adjacent subranges in these embodiments are selected to permit differentiation of the subranges by flow cytometry, and such selection will be readily apparent to those skilled in the use of and instrumentation for flow cytometry. In this specification, the term "mean diameter" refers to a number average diameter. In some embodiments, the subrange width is about ±5% CV or less of the mean diameter, where "CV" stands for "coefficient of variation" and is defined as the standard deviation of the particle diameter divided by the mean particle diameter, times 100 percent. The minimum spacing between mean diameters among the various subranges can vary depending on the microparticle size distribution, the ease of segregating microparticles by size for purposes of attaching different assay reagents, and the type and sensitivity of the flow cytometry equipment. In some embodiments, best results will be achieved when the mean diameters of different subranges are spaced apart by at least about 6% of the mean diameter of one of the subranges, e.g., at least about 8% of the mean diameter of one of the subranges, e.g., at least about 10% of the mean diameter of one of the subranges. In some embodiments, the standard deviation of the particle diameters within each subrange is less than one third of the separation of the mean diameters of adjacent subranges.

Another example of a differentiation parameter that can be used to distinguish among different groups of particles is fluorescence. Differentiation by fluorescence is accomplished by incorporating one or more fluorescent materials in the particles, the fluorescent materials having different fluorescent emission spectra and being distinguishable on this basis. Differentiation can be achieved by using fluorescent materials that have different fluorescence intensities or that emit fluorescence at different wavelengths, or by varying the amount of fluorescent material incorporated. Differentiation by fluorophores can also be achieved by using combinations of fluorophores for each particle subgroup. For example, the particle can be made to contain a red fluorochrome such as Cy5 together with a far-red fluorochrome such as Cy5.5, at different relative amounts for different subgroups. Additional fluorochromes can be used to further expand the system. Each microparticle can thus contain a plurality of fluorescent dyes at varying wavelengths.

By using fluorescence emissions at different wavelengths, the wavelength difference can be used to distinguish the particle groups from each other, while also distinguishing the labels in the labeled anti-human antibodies from the labels that differentiate one particle group from another. An example of a fluorescent substance that can be used as a means of distinguishing particle groups is fluorescein and an example of a substance that can be used for the assay detection is phycoerythrin. In the use of this example, different particle groups can be dyed with differing concentrations of fluorescein to distinguish them from each other, while phycoerythrin is used as the label on the various labeled binding members used in the assay.

Another example of a differentiation parameter that can be used to distinguish among the various groups of particles is light scatter. Side angle light scatter varies with particle size, granularity, absorbance and surface roughness, while forward angle light scatter is mainly affected by size and refractive index. Varying any of these qualities can result in light scatter differences that can serve as a means of distinguishing the various groups.

Still another example of a differentiation parameter is absorbance. When light is applied to particles, the absorbance of the light by the particles is indicated mostly by a change in the strength of the laterally (side-angle) scattered light while the strength of the forward-scattered light is relatively unaffected. Consequently, the difference in absorbance between various colored dyes associated with the particles is determined by observing differences in the strength of the laterally scattered light.

A still further example of a differentiation parameter is the number of particles in each group. When the number of particles in each group is varied in a known way, the count of particles having various assay responses can be associated with a particular assay by the number of particles having each response.

As the above examples illustrate, a wide array of parameters or characteristics can be used as differentiation parameters to distinguish the particles of one group from those of another. The differentiation parameters may arise from particle size, from particle composition, from particle physical characteristics that affect light scattering, from excitable fluorescent dyes or colored dyes that impart different emission spectra and/or scattering characteristics to the particles, or from different concentrations of one or more fluorescent dyes. When the distinguishable particle parameter is a fluorescent dye or color, it can be coated on the surface of the particle, embedded in the particle, or bound to the molecules of the particle material. Thus, fluorescent particles can be manufactured by combining the polymer material with the fluorescent dye, or by impregnating the particle with the dye. Particles with dyes already incorporated and thereby suitable for use in the present invention are commercially available, from suppliers such as Spherotech, Inc. (Libertyville, Ill., USA) and Molecular Probes, Inc. (Eugene, Oreg., USA).

When particles are used, particularly microparticles, the use of flow cytometry is a convenient way of sorting the particles by the differentiation parameter, and also in many cases of determining whether a label has been attached to the particle through the assay components as a result of the assay reaction.

Methods of, and instrumentation for, flow cytometry are known in the art, and can be used in the practice of the present invention. Flow cytometry in general resides in the passage of a suspension of particles (or cells) in as a stream through a light beam and coupled to electro-optical sensors, in such a manner that only one particle at a time passes the region of the sensors. As each particle passes this region, the light beam is perturbed by the presence of the particle, and the resulting scattered and fluoresced light are detected. The optical signals are used by the instrumentation to identify the subgroup to which each particle belongs, along with the presence and amount of label, so that individual assay results are achieved. Descriptions of instrumentation and methods for flow cytometry are found in the literature. Examples are McHugh, "Flow Microsphere Immunoassay for the Quantitative and Simultaneous Detection of Multiple Soluble Analytes," Methods in Cell Biology 42, Part B (Academic Press, 1994); McHugh et al., "Microsphere-Based Fluorescence Immunoassays Using Flow Cytometry Instrumentation," Clinical Flow Cytometry, Bauer, K. D., et al., eds. (Baltimore, Md., USA: Williams and Williams, 1993), pp. 535-544; Lindmo et al., "Immunometric Assay Using Mixtures of Two Particle Types of Different Affinity," J. Immunol. Meth. 126: 183-189 (1990); McHugh, "Flow Cytometry and the Application of Microsphere-Based Fluorescence Immunoassays," Immunochemica 5: 116 (1991); Horan et al., "Fluid Phase Particle Fluorescence Analysis: Rheumatoid Factor Specificity Evaluated by Laser Flow Cytophotometry," Immunoassays in the Clinical Laboratory, 185-189 (Liss 1979); Wilson et al., "A New Microsphere-Based Immunofluorescence Assay Using Flow Cytometry," J. Immunol. Meth. 107: 225-230 (1988); Fulwyler et al., "Flow Microsphere Immunoassay for the Quantitative and Simultaneous Detection of Multiple Soluble Analytes," Meth. Cell Biol. 33: 613-629 (1990); Coulter Electronics Inc., United Kingdom Patent No. 1,561,042 (published Feb. 13, 1980); and Steinkamp et al., Review of Scientific Instruments 44(9): 1301-1310 (1973).

The methods of the present invention, and the kits of the present invention that contain materials for use in practicing the methods, allow for the simultaneous detection and optionally quantification of the various analytes in a biological sample. The presence of these analytes or panel of analytes can be an indication of the presence, absence, or stage of a biological condition in the subject from whom the sample was taken. In some embodiments, the detection and/or quantification of some or all of the various analytes in a sample is used to provide a prognosis or to assess the efficacy of a pharmaceutical treatment (e.g., an anti-viral drug). Diagnosis, prognosis, or assessing pharmaceutical efficacy can be achieved for example by correlating the amounts of certain analytes in the sample with known amounts associated with healthy individuals, diseased individuals, or both. In some embodiments, the diagnosis or prognosis can be used to recommend a course of treatment for the subject.

In another embodiment, the normalization factor can be used to normalize signal values as assay reagents degrade over time. For example, the SNB signal (like the assay signal) is sensitive to concentrations of both the biotinylated conjugate and the streptavidin-phycoerythrin (SA-PE) reagent. As these reagents degrade on storage or under elevated temperature associated with shipping stress, a loss of signal is typically observed for both the SNB and the assay bead. Using SNB normalization maintains the assay response stability despite the absolute loss of assay signal. This has advantages for assay sensitivity related to calibration curve slope.

EXAMPLES

Example 1

This example demonstrates that a hFXIII bead included in an HIV detection assay can be used to detect unexpected and unacceptable variations in assay signal.

Methods:

All incubations are at 37° C. 25 µL of bead reagent containing beads for detection of HIV analytes, hFXIII, SVB, and ISB, and 25 µL sample are incubated for 28.5 min, then washed. 50 µL of Conjugate 1 reagent containing biotinylated conjugates is added to the beads and incubated 10 min, then washed. 25 µL Conjugate 2 containing concentrated SA-PE and 25 µL wash fluid are added to the beads and incubated 10 min. After washing, beads are resuspended in 50 µL wash fluid and sent to the detector. Beads are in a buffer containing triethanolamine and CHAPS (3[(3-Cholamidopropyl)dimethylammonio]-propanesulfonic acid), protein stabilizers, blockers, and preservatives. Conjugate 1 and Conjugate 2 are in phosphate buffer with NaCl, protein stabilizers, blockers, and preservatives. All buffers are pH 7-7.4. The starting concentration of Streptavidin-PE was 4-8 µg/mL in the reagent. During reaction vessel processing, 25 µL of Streptavidin-PE reagent was mixed with 25 µL of diluent for a final working concentration of 2-4 µg/mL.

Biological samples containing HIV antigen (p24 antigen) were incubated with magnetic beads covalently coupled to anti-p24 antibodies and with magnetic beads covalently coupled to hFXIII (referred to herein as a hFXIII bead or signal normalization bead (SNB)). Following the incubation step, the beads were separated from the sample, washed, and incubated with biotinylated antibodies that specifically bind p24 antigen and hFXIII (mouse anti-human FXIII-biotin). The concentration of biotin conjugated anti-p24 antibody was 5.0 µg/mL. The concentration of biotin conjugated anti-p24 antibody was 1.5 µg/mL. Excess conjugate was removed by washing, and streptavidin-PE conjugate was added to the beads. Following incubation with streptavidin-PE, the beads were washed and the amount of fluorescent signal was detected. Twelve (12) replicate assays were performed.

As shown in FIG. 1, the amount of HIV antigen signal and the amount of hFXIII signal were positively correlated for each replicate. Further, the normalized signal (antigen signal/hFXIII signal multiplied by 150) showed much less variability than the antigen signal between replicates. As shown in Table 2, the coefficient of variation (percent relative standard deviation, CV %) was much less using the normalized signal than either the antigen signal or hFXIII signal. Further, the hFXIII signal can be used to detect an invalid assay result, such as when the hFXIII signal falls below a preset limit (e.g., a signal for hFXIII below 250).

TABLE 2

Analysis of 12 Replicates of Antigen Positive Sample

| Replicate ID | Antigen | hFXIII | Normalized |
|---|---|---|---|
| 1 | 239.0 | 338.5 | 105.9 |
| 2 | 248.0 | 359.0 | 103.6 |
| 3 | 257.0 | 351.5 | 109.7 |
| 4 | 263.0 | 337.5 | 116.9 |
| 5 | 248.0 | 348.0 | 106.9 |
| 6 | 145.0 | 200.0 | 108.8 |
| 7 | 253.0 | 348.5 | 108.9 |
| 8 | 270.0 | 424.0 | 95.5 |
| 9 | 238.0 | 320.5 | 111.4 |
| 10 | 250.0 | 360.5 | 104.0 |
| 11 | 247.0 | 344.5 | 107.5 |
| 12 | 267.0 | 362.0 | 110.6 |
| Mean | 243.8 | 341.2 | 107.5 |
| Std Dev | 32.7 | 51.0 | 5.2 |
| CV % | 13.4 | 14.9 | 4.8 |

This example demonstrates that using a hFXIII bead to normalize analyte values produced improved assay precision. This example further demonstrates that the hFXIII signal normalization bead can be used as a control bead to detect an invalid assay.

Example 2

This example demonstrates that using a hFXIII bead significantly improves the CV of the normalized signal when performing replicates of a multiplex control sample.

A multiplex control sample containing human polyclonal antibodies for HIV-1 and HIV-2 as well as rabbit monoclonal antibodies representing HIV-O was incubated with magnetic beads covalently coupled to antigens that specifically bind to the antibodies (target analyte beads). The HIV-1 detection bead was ligated to GP-160. The HIV-2 detection bead was ligated to SPOH. The HIV-O detection bead was ligated to AFR. The control sample was also incubated with hFXIII beads. The sample was processed as described in Example 1. Five (5) replicates of the assay were performed.

Figure 2:
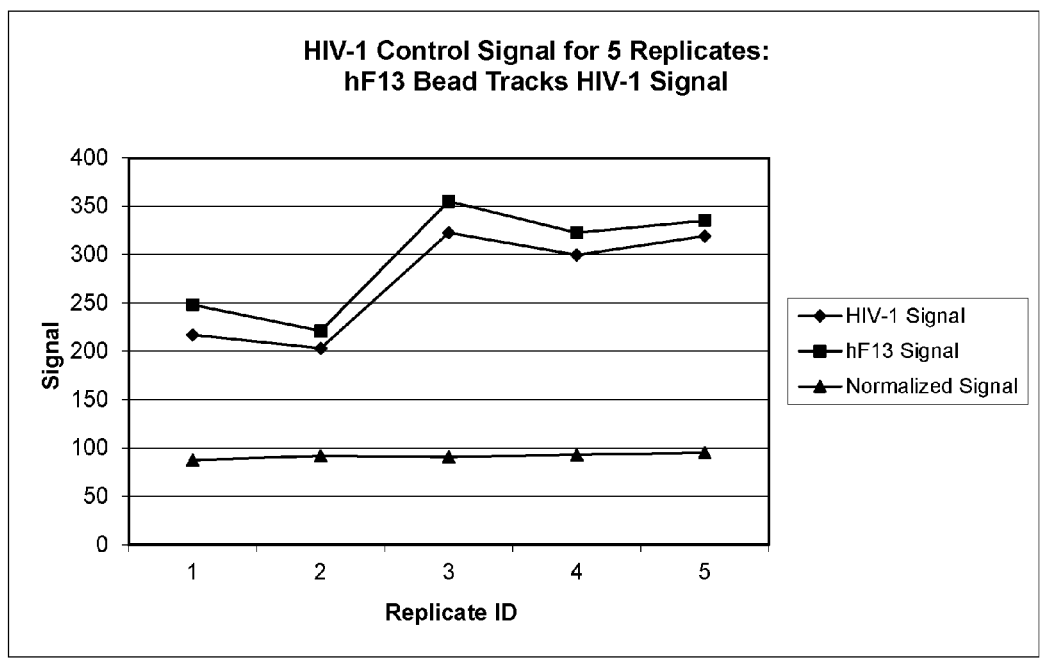
FIG. 2 illustrates the use of a human Factor XIII coated bead as a control and to produce a normalized signal in a representative multiplex HIV control assay that detects human polyclonal antibodies to HIV-1. Five (5) replicates were performed, and the data was normalized as described in Example 2.

As shown in FIG. 2, the HIV-1 control signal was positively correlated with the hFXIII signal in each replicate. The normalized signal showed much less variation between replicates. As shown in Table 3, the CV % of the normalized signal was significantly lower that the CV % of either the HIV-1 signal or the hFXIII signal.

TABLE 3

Analysis of five replicates of HIV-1 antibody positive control sample.

HIV-1

| | | HIV-1 | hFXIII | Normalized Signal |
|---|---|---|---|---|
| 1 | L03-QC | 217 | 248 | 87.5 |
| 2 | L03-QC | 203 | 221 | 91.9 |
| 3 | L03-QC | 323 | 355 | 90.8 |
| 4 | L03-QC | 300 | 323 | 92.9 |
| 5 | L03-QC | 319 | 335 | 95.2 |
| | Mean | 272 | 296 | 92 |
| | Std Dev | 57.7 | 58.4 | 2.8 |
| | CV % | 21.2 | 19.7 | 3.1 |

Figure 3:
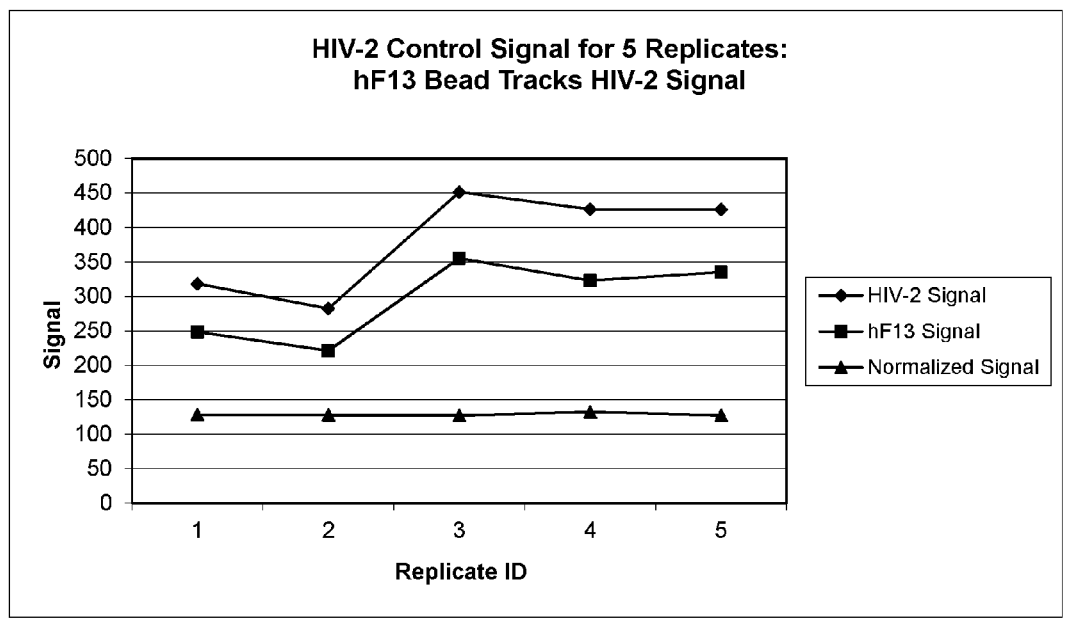
FIG. 3 illustrates the use of a human Factor XIII coated bead as a control and to produce a normalized signal in a representative multiplex HIV control assay that detects human polyclonal antibodies to HIV-2. Five (5) replicates were performed, and the data was normalized as described in Example 2.

Similarly, FIG. 3 shows that the HIV-2 control signal was positively correlated with the hFXIII signal in each replicate. The normalized signal showed much less variation between replicates. Table 4 shows that the CV % of the normalized signal was significantly lower that the CV % of either the HIV-2 signal or the hFXIII signal.

TABLE 4

Analysis of five replicates of HIV-2 antibody positive control sample.

HIV-2

| | | HIV-2 | hFXIII | Normalized Signal |
|---|---|---|---|---|
| 1 | L03-QC | 318 | 248 | 128.2 |
| 2 | L03-QC | 282 | 221 | 127.6 |
| 3 | L03-QC | 451 | 355 | 127.0 |
| 4 | L03-QC | 426 | 323 | 132.1 |
| 5 | L03-QC | 426 | 335 | 127.2 |
| | Mean | 381 | 296 | 128 |
| | Std Dev | 75.4 | 58.4 | 2.1 |
| | CV % | 19.8 | 19.7 | 1.6 |

Figure 4:
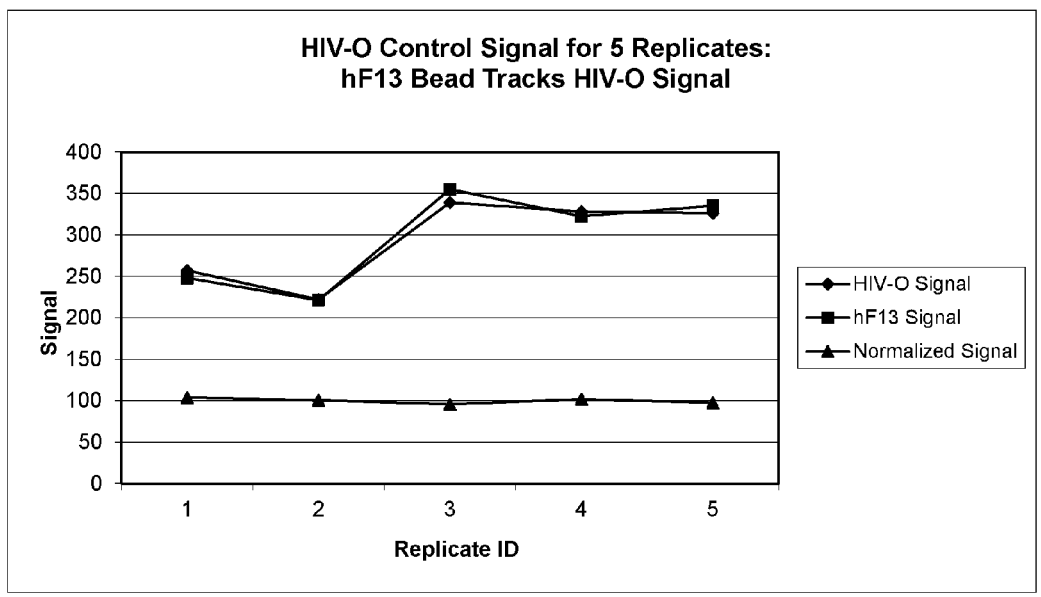
FIG. 4 illustrates the use of a human Factor XIII coated bead as a control and to produce a normalized signal in a representative multiplex HIV control assay that detects rabbit monoclonal antibodies to HIV-O. Five (5) replicates were performed, and the data was normalized as described in Example 2.

Similar results were obtained with the HIV-O control sample. FIG. 4 shows that the HIV-O control signal was positively correlated with the hFXIII signal in each replicate. The normalized signal showed much less variation between replicates. Table 5 shows that the CV % of the normalized signal was significantly lower that the CV % of either the HIV-O signal or the hFXIII signal.

TABLE 5

Analysis of five replicates of HIV-O antibody positive control sample.

HIV-O

| | | HIV-O | hFXIII | Normalized Signal |
|---|---|---|---|---|
| 1 | L03-QC | 257 | 248 | 103.6 |
| 2 | L03-QC | 222 | 221 | 100.5 |
| 3 | L03-QC | 339 | 355 | 95.5 |
| 4 | L03-QC | 328 | 323 | 101.7 |
| 5 | L03-QC | 326 | 335 | 97.3 |
| | Mean | 294 | 296 | 100 |
| | Std Dev | 51.9 | 58.4 | 3.3 |
| | CV % | 17.6 | 19.7 | 3.3 |

Example 3

This example describes factors that influence the final fluorescent signal generated on the beads.

During development of the above assays, it was observed that replicate analysis of samples such as calibrators, controls or patient specimens (serum or plasma) could occasionally produce variable fluorescent signals on the assay beads resulting in high coefficients of variation. In some cases, the signal variation could be as high as 50% or more and was sufficient to produce a response classified as positive for some replicates but negative for others.

Numerous factors associated with assay chemistry as well as manual or automated sample processing are responsible for the magnitude of the final fluorescent signal generated on the beads. Some sources of signal fluctuation between replicates can be related to assay variations listed in Table 6.

Table 6. Factors that introduce signal fluctuation between replicates.

Step-1 Bead-Sample variations
    sample dispense volume
    bead dispense volume
    bead-sample incubation time
    bead-sample mixing efficiency
    bead-sample incubation temperature
    bead-sample washing efficiency to remove bulk sample after analyte binding to beads
    Volume of residual wash reagent after bead-sample wash steps Step-2 Bead-Conjugate variations
    Biotin conjugate concentration
    Biotin conjugate volume
    bead-conjugate incubation time
    bead-conjugate mixing efficiency
    bead-conjugate incubation temperature
    bead-conjugate washing efficiency to remove bulk conjugate after conjugate binding to beads
    Volume of residual wash reagent after bead-conjugate wash steps Step-3 Bead-PE variations
    PE dispense volume
    bead-PE incubation time
    bead-PE mixing efficiency
    bead-PE incubation temperature
    bead-PE washing efficiency to remove bulk PE after analyte binding to beads and prior to detection
    time from bead-PE binding to fluorescent detection
    Detector response (drift) due to temperature or voltage over time Since hFXIII is covalently coupled to beads, it is not responsive to variations in the analyte-bead binding steps described in Step-1. It is however responsive to the final process shown in Step-1 (volume of residual wash reagent after bead-sample wash steps) as this affects the final concentration of biotin reagent added in Step-2. The bead is responsive to other processes listed in Steps 2 and Step 3.

Example 4

This example demonstrates that normalization of signal values using the hFXIII signal normalization bead reduces variation between replicates compared to an internal standard bead coated with tetramethylcadaverine rhodamine (TMRC).

Since the fluorecence detector response may drift over time, some manual or automated assays typically include an Internal Standard Bead (ISB) coated with a fixed amount of TMRC, thus producing a standard amount of signal. Assay signals can be normalized to the ISB signal to compensate for detector variation. However, since ISB does not participate in the immunoassay, it does not respond to potential process variations described in Table 6 other than detector drift. For a series of replicates, no improvement in assay precision was observed when normalizing signals to ISB as shown below in Table 7 for the HIV-1 data described above in Example 2.

TABLE 7

Comparison of the normalized signal using an ISB and hFXIII SNB.

| Replicate | Accession | HIV-1 Raw Signal | hF13 Raw Signal | ISB Raw Signal | HIV-1/ISB *8000 Normalized Signal | HIV-1/hF13*100 Normalized Signal |
|---|---|---|---|---|---|---|
| 1 | L03-QC | 217 | 248 | 8201 | 212 | 87.5 |
| 2 | L03-QC | 203 | 221 | 8137 | 200 | 91.9 |
| 3 | L03-QC | 323 | 355 | 8147 | 317 | 90.8 |
| 4 | L03-QC | 300 | 323 | 7935 | 302 | 92.9 |
| 5 | L03-QC | 319 | 335 | 8027.5 | 318 | 95.2 |
|  | Mean | 272 | 296 | 8090 | 270 | 92 |
|  | Std Dev | 57.7 | 58.4 | 106.9 | 58.9 | 2.8 |
|  | CV % | 21.2 | 19.7 | 1.3 | 21.8 | 3.1 |

Example 5

This example demonstrates that signal variation is affected by residual biotin conjugate in the reaction vessel prior to addition of streptavidin-PE.

Figure 5:
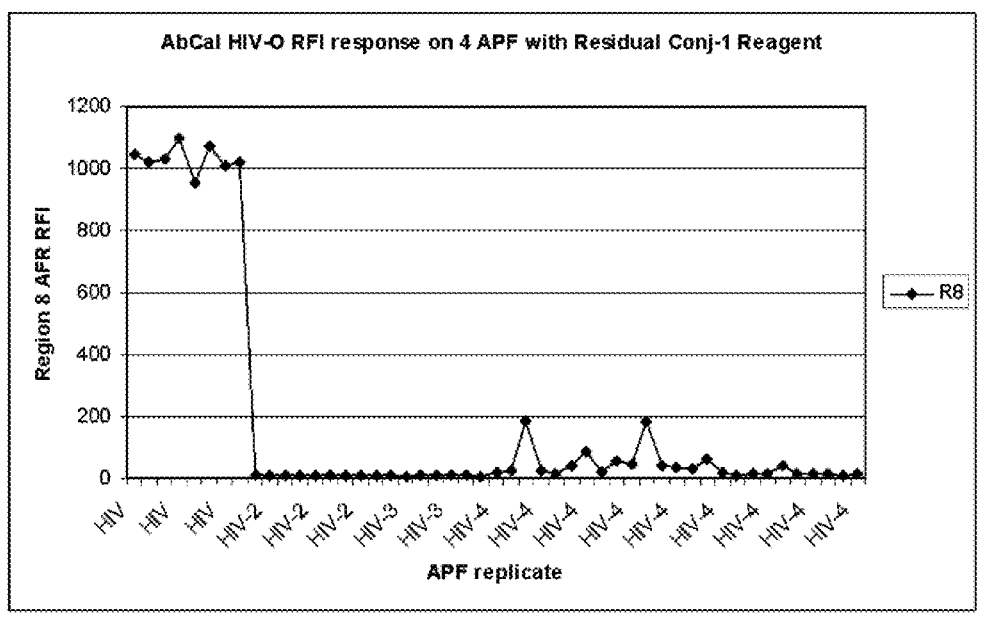
FIG. 5 illustrates that the assay signal is decreased by various amounts of biotin conjugate remaining in the reaction vessel in a representative experiment that detects antibodies to HIV-O, as described in Example 5.

The inventors observed that if biotin conjugate is not efficiently removed during wash phase of Step 2 in Table 6 (e.g., due to instrument wash-aspirate errors), signal is significantly reduced due to the interaction of residual aqueous biotin conjugate with PE. The result is an effective reduction in PE concentration. This type of error is modeled below for HIV-O antibody detection in antibody calibrator:

Four test methods (labeled HIV, HIV2, HIV3, HIV4 on the X axis) were created in which various amounts of biotin conjugate were purposefully left in the reaction vessel (RV) prior to the addition of the fluorescent reporter (PE). FIG. 5 shows the signal response for the test methods.

HIV represents the standard method with full RV washing protocol (8 replicates shown). HIV-2 and HIV-3 show the complete loss of signal when 10 µL or 5 µL, respectively, of residual biotin conjugate are purposefully added to the RV prior to the addition of PE reagent. HIV-4 shows the effect of poor incomplete washing of the RV prior to the addition of the PE reagent. The ISB signal remained constant (data not shown).

In separate experiments exploring the use of an alternate internal standard bead coupled directly with biotin, it was found that if the biotin bead was added in sufficient quantity (ie solid phase biotin), the assay signals will also drop. The ISB does not detect this drop in assay signals, but since it appears to be an effect on free PE concentration, the SNB tracks the assay signal producing good precision.

Likewise, if biotin conjugate dispense volume is lower than expected due to instrument pipetting error, or if residual wash volume is higher than expected due to instrument wash aspirate error, the final conjugate concentration in the reaction mixture is reduced resulting in lower assay signal and lower hFXIII signal while the ISB signal remains constant.

In summary, this example demonstrates that the hFXIII SNB can be used to normalize the assay signal when residual biotin conjugate remains in the reaction vessel prior to the addition of labeled streptavidin.

Example 6

This example demonstrates that biological matrix effects can produce variable recovery of p24 antigen signal, and that this variability is significantly reduced when using the hFXIII bead for normalization.

A human donor provided blood specimens drawn into 9 different types of collection tubes. The glass or plastic collection tubes contained various anticoagulants for production of serum or plasma. Serum was obtained from tubes without anticoagulant. Some tubes contain serum separator (SST) or plasma separator (PST) barriers for separation of cells from serum or plasma. The tube types are described below:

| Specimen Type | Anticoagulant | Glass | Plastic |
|---|---|---|---|
| Serum | None | x | x |
| Serum SST | None | x | x |
| Plasma | K2-EDTA |  | x |
| Plasma | Sodium Citrate |  | x |
| Plasma | Sodium Heparin |  | x |
| Plasma | Lithiujm Heparin |  | x |
| Plasma PST | Lithium Heparin |  | x |

Each serum or plasma matrix was supplemented with an identical concentration of HIV p24 antigen and tested with 5 replicates per condition according to the method in Example 1.

Figure 6:
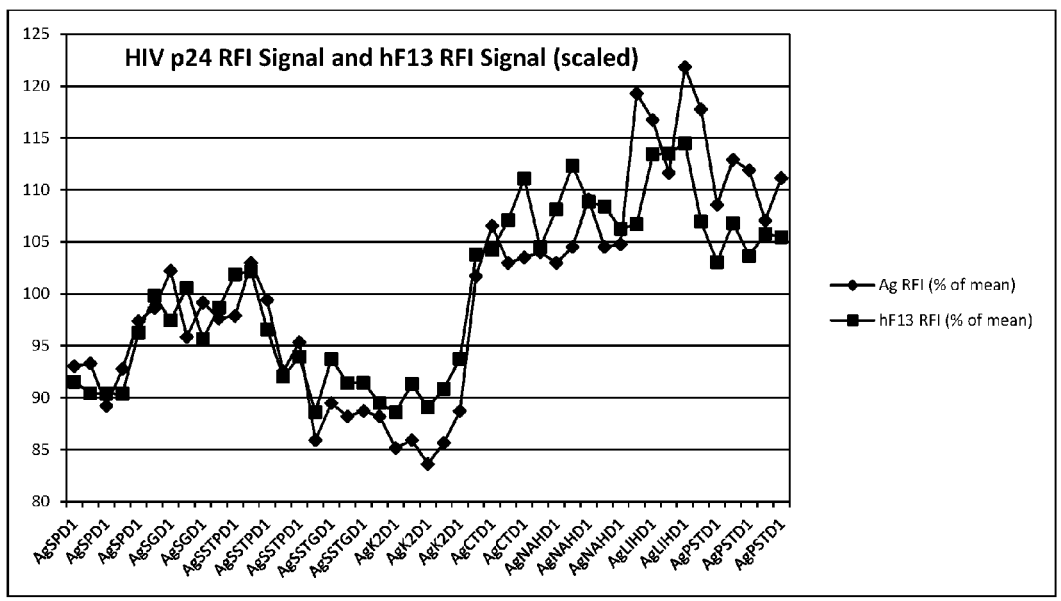
FIG. 6 illustrates a plot of the relative response of the HIV p24 antigen signal and human Factor XIII signal detected in serum and plasma samples from the same donor in various biological matrices supplemented with identical concentrations of HIV p24 antigen.
Figure 7:
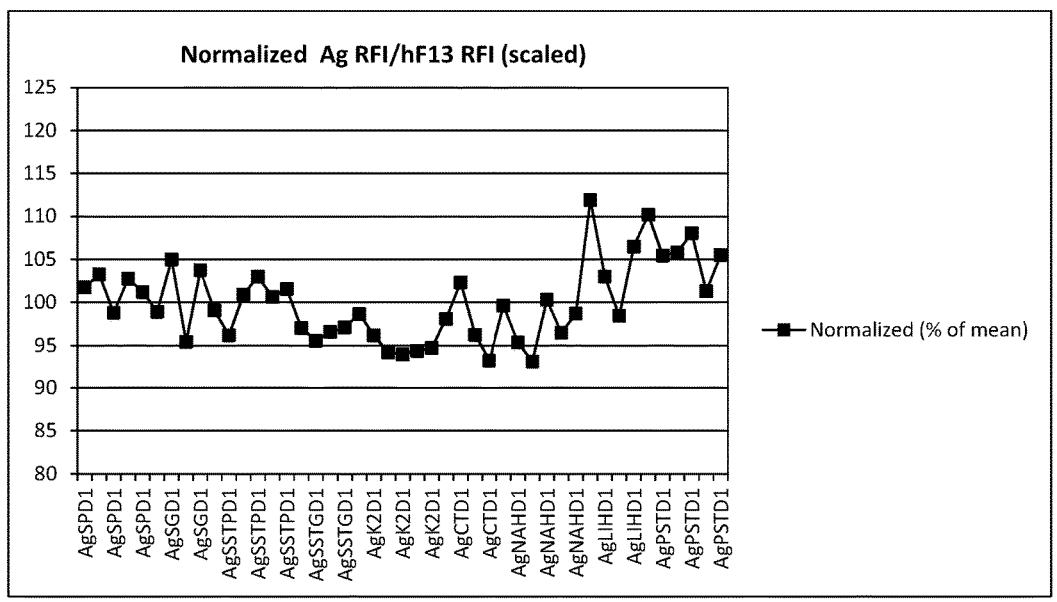
FIG. 7 illustrates a plot of the normalized signal from the same experiment as in FIG. 6, showing lower variation for all samples in different biological matrices.

In this example all replicates and sample matrix types were expected to produce the same response for Ag RFI. However, as shown in Table 8 and FIG. 6, there was substantial variation between the different matrix types. The % CV of the p24 antigen signal for all replicates and sample types was 10.1%. In contrast, when the data was normalized using hFXIII, the variability was significantly reduced. As shown in Table 8 and FIG. 7, the % CV for the normalized response (p24 signal/hFXIII signal) was improved to 4.6%.

TABLE 8

Detection of HIV p24 antigen RF1 in serum and plasma samples collected in different types of collection tubes and treated with different anticoagulants and normalized to signal from hFXIII.

| Description | ID | Replicate | Ag RFI Signal | Ag RFI (% of mean) | hFXIII RFI Signal | hFXIII RFI (% of mean) | Normalized (Ag RFI/hFXIII) | Normalized (% of mean) | TMRC RFI | TMRC RFI (% of mean) |
|---|---|---|---|---|---|---|---|---|---|---|
| Serum-Plastic | AgSPD1 | 1 | 183 | 93 | 2001 | 92 | 137 | 102 | 9280 | 96 |
| Serum-Plastic | AgSPD1 | 2 | 183 | 93 | 1977 | 90 | 139 | 103 | 9500 | 98 |

TABLE 8-continued

Detection of HIV p24 antigen RF1 in serum and plasma samples collected in different types of collection tubes and treated with different anticoagulants and normalized to signal from hFXIII.

| | | | | | | | | | | |
|---|---|---|---|---|---|---|---|---|---|---|
| Serum-Plastic | AgSPD1 | 3 | 175 | 89 | 1976 | 90 | 133 | 99 | 9604 | 99 |
| Serum-Plastic | AgSPD1 | 4 | 182 | 93 | 1976 | 90 | 138 | 103 | 9521 | 98 |
| Serum-Plastic | AgSPD1 | 5 | 191 | 97 | 2105 | 96 | 136 | 101 | 9495 | 98 |
| Serum-Glass | AgSGD1 | 1 | 194 | 99 | 2182 | 100 | 133 | 99 | 9729 | 101 |
| Serum-Glass | AgSGD1 | 2 | 201 | 102 | 2130 | 97 | 141 | 105 | 9284 | 96 |
| Serum-Glass | AgSGD1 | 3 | 188 | 96 | 2198 | 101 | 128 | 95 | 9886 | 102 |
| Serum-Glass | AgSGD1 | 4 | 195 | 99 | 2091 | 96 | 140 | 104 | 9591 | 99 |
| Serum-Glass | AgSGD1 | 5 | 192 | 98 | 2157 | 99 | 133 | 99 | 10016 | 104 |
| Serum-SST-Plastic | AgSSTPD1 | 1 | 192 | 98 | 2227 | 102 | 129 | 96 | 9498 | 98 |
| Serum-SST-Plastic | AgSSTPD1 | 2 | 202 | 103 | 2233 | 102 | 136 | 101 | 9758 | 101 |
| Serum-SST-Plastic | AgSSTPD1 | 3 | 195 | 99 | 2112 | 97 | 139 | 103 | 9892 | 102 |
| Serum-SST-Plastic | AgSSTPD1 | 4 | 182 | 93 | 2012 | 92 | 135 | 101 | 9390 | 97 |
| Serum-SST-Plastic | AgSSTPD1 | 5 | 187 | 95 | 2054 | 94 | 137 | 102 | 9724 | 100 |
| Serum-SST-Glass | AgSSTGD1 | 1 | 169 | 86 | 1937 | 89 | 130 | 97 | 9588 | 99 |
| Serum-SST-Glass | AgSSTGD1 | 2 | 176 | 89 | 2049 | 94 | 128 | 96 | 9523 | 98 |
| Serum-SST-Glass | AgSSTGD1 | 3 | 173 | 88 | 1999 | 91 | 130 | 97 | 9470 | 98 |
| Serum-SST-Glass | AgSSTGD1 | 4 | 174 | 89 | 1999 | 91 | 131 | 97 | 9640 | 100 |
| Serum-SST-Glass | AgSSTGD1 | 5 | 173 | 88 | 1956 | 89 | 133 | 99 | 9510 | 98 |
| Plasma-K2 EDTA | AgK2D1 | 1 | 167 | 85 | 1937 | 89 | 129 | 96 | 9582 | 99 |
| Plasma-K2 EDTA | AgK2D1 | 2 | 169 | 86 | 1996 | 91 | 127 | 94 | 9523 | 98 |
| Plasma-K2 EDTA | AgK2D1 | 3 | 164 | 84 | 1947 | 89 | 126 | 94 | 10026 | 104 |
| Plasma-K2 EDTA | AgK2D1 | 4 | 168 | 86 | 1986 | 91 | 127 | 94 | 9594 | 99 |
| Plasma-K2 EDTA | AgK2D1 | 5 | 174 | 89 | 2050 | 94 | 127 | 95 | 10023 | 104 |
| Plasma-Citrate | AgCTD1 | 1 | 200 | 102 | 2269 | 104 | 132 | 98 | 9873 | 102 |
| Plasma-Citrate | AgCTD1 | 2 | 209 | 107 | 2278 | 104 | 138 | 102 | 9913 | 102 |
| Plasma-Citrate | AgCTD1 | 3 | 202 | 103 | 2342 | 107 | 129 | 96 | 10146 | 105 |
| Plasma-Citrate | AgCTD1 | 4 | 203 | 103 | 2429 | 111 | 125 | 93 | 9578 | 99 |
| Plasma-Citrate | AgCTD1 | 5 | 204 | 104 | 2284 | 104 | 134 | 100 | 9631 | 100 |
| Plasma NaHeparin | AgNAHD1 | 1 | 202 | 103 | 2364 | 108 | 128 | 95 | 10032 | 104 |
| Plasma NaHeparin | AgNAHD1 | 2 | 205 | 105 | 2456 | 112 | 125 | 93 | 9700 | 100 |
| Plasma NaHeparin | AgNAHD1 | 3 | 214 | 109 | 2380 | 109 | 135 | 100 | 10073 | 104 |
| Plasma NaHeparin | AgNAHD1 | 4 | 205 | 105 | 2371 | 108 | 130 | 96 | 9577 | 99 |
| Plasma NaHeparin | AgNAHD1 | 5 | 206 | 105 | 2323 | 106 | 133 | 99 | 9654 | 100 |
| Plasma LiHeparin | AgLIHD1 | 1 | 234 | 119 | 2333 | 107 | 150 | 112 | 9802 | 101 |
| Plasma LiHeparin | AgLIHD1 | 2 | 229 | 117 | 2480 | 113 | 139 | 103 | 9779 | 101 |
| Plasma LiHeparin | AgLIHD1 | 3 | 219 | 112 | 2482 | 113 | 132 | 98 | 9796 | 101 |
| Plasma LiHeparin | AgLIHD1 | 4 | 239 | 122 | 2504 | 115 | 143 | 106 | 9545 | 99 |
| Plasma LiHeparin | AgLIHD1 | 5 | 231 | 118 | 2338 | 107 | 148 | 110 | 9530 | 98 |
| Plasma LiHeparin PST | AgPSTD1 | 1 | 213 | 109 | 2253 | 103 | 142 | 105 | 9839 | 102 |
| Plasma LiHeparin PST | AgPSTD1 | 2 | 222 | 113 | 2336 | 107 | 142 | 106 | 9458 | 98 |
| Plasma LiHeparin PST | AgPSTD1 | 3 | 220 | 112 | 2266 | 104 | 145 | 108 | 9827 | 102 |
| Plasma LiHeparin PST | AgPSTD1 | 4 | 210 | 107 | 2313 | 106 | 136 | 101 | 9426 | 97 |
| Plasma LiHeparin PST | AgPSTD1 | 5 | 218 | 111 | 2305 | 105 | 142 | 105 | 9656 | 100 |

| | Ag RFI Signal | Ag RFI (% of mean) | hFXIII RFI Signal | hFXIII RFI (% of mean) | Normalized (RFI/hFXIII) | Normalized (% of mean) | TMRC RFI | TMRC RFI (% of mean) |
|---|---|---|---|---|---|---|---|---|
| Signal | 196.2 | 100.0 | 2186.3 | 100.0 | 134.5 | 100.0 | 9677.2 | 100.0 |
| Stdev | 19.8 | 10.1 | 174.9 | 8.0 | 6.2 | 4.6 | 212.6 | 2.2 |
| % CV | 10.1 | 10.1 | 8.0 | 8.0 | 4.6 | 4.6 | 2.2 | 2.2 |

This example shows that using hFXIII to normalize the signal significantly reduced the variability associated with different matrix effects.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A kit for correcting for variations in sample processing and/or biological matrix effects when performing biological assays, said kit comprising human blood coagulation Factor XIII (hFXIII) immobilized on a solid support, and
 a plurality of solid supports having binding members immobilize thereon that bind an analyte in a sample, wherein the plurality of solid supports are divided into subpopulations that are differentiable from each other by a differentiation parameter comprising a characteristic that is independent of the binding members immobilized on the solid supports, and the binding members immobilized on each subpopulation are capable of binding to one analyte in the sample,
 wherein the solid support and/or the plurality of solid supports is selected from the wall or floor of an assay vessel, a dipstick, particles inside or suspended in an assay vessel, a bead, a magnetic bead, or a microparticle formed of a polymeric material.

2. The kit of claim 1, wherein hFXIII does not bind an analyte from a biological sample.

3. The kit of claim 1, further comprising an antibody to human Factor XIII immobilized on a solid support.

4. The kit of claim 1, further comprising tetramethylcadaverine rhodamine (TMRC) immobilized on a solid support.

5. The kit of claim 1, wherein the solid support and/or the plurality of solid supports is a bead or magnetic bead.

6. A composition for correcting for variations in sample processing and/or biological matrix effects when performing biological assays, said composition comprising hFXIII coupled to a solid support, and
 a plurality of solid supports having binding members immobilize thereon that bind an analyte in a sample, wherein the plurality of solid supports are divided into subpopulations that are differentiable from each other by a differentiation parameter comprising a characteristic that is independent of the binding members immobilized on the solid supports, and the binding members immobilized on each subpopulation are capable of binding to one analyte in the sample,
 wherein the solid support and/or the plurality of solid supports is selected from the wall or floor of an assay vessel, a dipstick, particles suspended in an assay vessel, a bead, a magnetic bead, or a microparticle formed of a polymeric material.

7. The composition of claim 6, wherein hFXIII does not bind an analyte from a biological sample.

8. The composition of claim 6, further comprising an antibody to human Factor XIII immobilized on a solid support.

9. The composition of claim 6, further comprising tetramethylcadaverine rhodamine (TMRC) immobilized on a solid support.

10. The composition of claim 6, wherein the solid support and/or the plurality of solid supports is a bead or magnetic bead.

11. The kit of claim 1, wherein the characteristic is selected from particle size, particle diameter, particle composition, light scatter, absorbance, number of particles, fluorescent dyes or colored dyes that impart different emission spectra and/or scattering characteristics to the solid supports, or from different concentrations of one or more fluorescent dyes.

12. The composition of claim 6, wherein the characteristic is selected from particle size, particle diameter, particle composition, light scatter, absorbance, number of particles, fluorescent dyes or colored dyes that impart different emission spectra and/or scattering characteristics to the solid supports, or from different concentrations of one or more fluorescent dyes.

* * * * *